United States Patent
Sohn et al.

(10) Patent No.: US 9,488,567 B2
(45) Date of Patent: Nov. 8, 2016

(54) PIPE DAMAGE DETECTION APPARATUS AND METHOD

(75) Inventors: Hoon Sohn, Daejeon (KR); Hyeon Seok Lee, Daejeon (KR); Jin Yeol Yang, Daejeon (KR)

(73) Assignee: KOREA ADVANCED INSTITUTE OF SCIENCE AND TECHNOLOGY (KR)

(*) Notice: Subject to any disclaimer, the term of this patent is extended or adjusted under 35 U.S.C. 154(b) by 190 days.

(21) Appl. No.: 14/373,115

(22) PCT Filed: Jan. 20, 2012

(86) PCT No.: PCT/KR2012/000568
§ 371 (c)(1),
(2), (4) Date: Jul. 18, 2014

(87) PCT Pub. No.: WO2013/108948
PCT Pub. Date: Jul. 25, 2013

(65) Prior Publication Data
US 2014/0366634 A1    Dec. 18, 2014

(30) Foreign Application Priority Data
Jan. 20, 2012   (KR) .................. 10-2012-0006709

(51) Int. Cl.
*G01N 21/17* (2006.01)
*G01N 29/34* (2006.01)
(Continued)

(52) U.S. Cl.
CPC ............ *G01N 21/1702* (2013.01); *G01M 3/38* (2013.01); *G01N 29/04* (2013.01); *G01N 29/041* (2013.01);
(Continued)

(58) Field of Classification Search
CPC ........... G01N 29/041; G01N 29/2418; G01N 29/34; G01N 29/04; G01N 21/1702; G01N 2291/0289; G01N 2291/2634; G01N 2201/067; G01N 2021/1706; G01N 2201/08; G01M 3/38

USPC ............................................... 73/643
See application file for complete search history.

(56) References Cited

U.S. PATENT DOCUMENTS 5,790,620 A *   8/1998   Okazaki ............. B23K 26/0069
                                                                134/1
8,593,627 B2 *  11/2013  Crann, Jr. ............ G01N 21/954
                                                              356/241.1
(Continued)

FOREIGN PATENT DOCUMENTS

JP   63-302358   9/1988
JP   07-034371   6/1995
(Continued)

OTHER PUBLICATIONS

PCT/KR2012/000568—International File Date: Jan. 20, 2012—International Search Report: Korea Advanced Institute of Science and Technology; 3 pgs.

*Primary Examiner* — J M Saint Surin
(74) *Attorney, Agent, or Firm* — Schmeiser, Olsen & Watts, LLP (57) ABSTRACT

A pipe damage detection apparatus and method are disclosed. The pipe damage detection apparatus includes an ultrasonic supply unit configured to supply an ultrasonic signal to a pipe; an ultrasonic reception unit configured to receive the ultrasonic signal of the pipe; and an analysis unit configured to analyze the ultrasonic signal received by the ultrasonic reception unit, and determine whether the pipe is damaged. The pipe damage detection apparatus and method can detect whether a pipe that is difficult for an inspector to access because it is coated with an insulating material or buried in the ground is damaged.

6 Claims, 7 Drawing Sheets

(51) Int. Cl.
  *G01N 29/04* (2006.01)
  *G01M 3/38* (2006.01)
  *G01N 29/24* (2006.01)

(52) U.S. Cl.
  CPC .......... *G01N 29/2418* (2013.01); *G01N 29/34* (2013.01); *G01N 2021/1706* (2013.01); *G01N 2201/067* (2013.01); *G01N 2201/08* (2013.01); *G01N 2291/0289* (2013.01); *G01N 2291/2634* (2013.01)

(56) References Cited

U.S. PATENT DOCUMENTS

2005/0162662 A1* 7/2005 Sauerland .......... G01B 11/0691
  356/502
2009/0257315 A1* 10/2009 Ko .......................... G01S 11/16
  367/135
2015/0068311 A1* 3/2015 Tanaka ................. G01N 29/043
  73/629

FOREIGN PATENT DOCUMENTS

| | | | |
|---|---|---|---|
| JP | 2006234722 | * | 7/2006 |
| JP | 2007-232528 | | 9/2007 |
| JP | 2008-076237 | | 4/2008 |
| JP | 2011-220801 | | 11/2011 |
| KR | 101072802 B1 | | 10/2011 |
| KR | 1424070 | * | 7/2014 |
| WO | 2013108948 A1 | | 7/2013 |

* cited by examiner

SIGNAL SAMENESS BETWEEN PATHS $A_i$ AND $B_i$

FIG.7

SIGNAL SAMENESS BETWEEN PATHS $A_i B_{i-1}$ AND $A_i B_{i+1}$

FIG.8

SIGNAL SAMENESS BETWEEN PATHS $A_i B_{i-2}$ AND $A_i B_{i+2}$

PIPE DAMAGE DETECTION APPARATUS AND METHOD

FIELD OF THE TECHNOLOGY

The following relates to a pipe damage detection apparatus and method, and more particularly, to a pipe damage detection apparatus and method capable of detecting whether underground pipes and inner pipes of nuclear power plant and chemical plant facilities are damaged.

BACKGROUND

Generally, infrastructure facilities such as bridges, large facilities, underground utilities, etc. are becoming larger and modernized according to the development of society in order to meet various requirements of members of society.

Accordingly, various new technologies, new methods, new materials, etc. are being introduced, and the need for verification of stability, etc., which is prerequisite for introducing them, is being required.

Recently, a laser ultrasonic apparatus is used to diagnose structures. The laser ultrasonic apparatus radiates a strong pulse laser beam on the surface of an object, generates an ultrasonic signal, and detects whether the object is damaged by measuring the ultrasonic signal propagated or reflected from the object.

Meanwhile, a technique serving as background to the present invention entitled "Inspection apparatus and method using laser" is disclosed in Korean Patent No. 10-1072802 registered on Oct. 6, 2011.

SUMMARY

An aspect relates to a pipe damage detection apparatus and method capable of safely detecting whether a pipe with a high temperature condition used in nuclear power generation facilities and plant facilities or underground pipes is damaged.

According to another aspect, there is provided a pipe damage detection apparatus, including: an ultrasonic supply unit configured to supply an ultrasonic signal to a pipe; an ultrasonic reception unit configured to receive the ultrasonic signal of the pipe; and an analysis unit configured to analyze the ultrasonic signal received by the ultrasonic reception unit, and determine whether the pipe is damaged.

The ultrasonic supply unit may include: a generation unit configured to generate a laser beam; a supply unit including one end which is connected to the generation unit, and configured to supply the laser beam; and a guide unit connected to the other end of the supply unit, mounted on the pipe, and configured to guide the laser beam to the pipe.

The supply unit may be an optical fiber.

The guide unit may include: a guide pipe connected to the supply unit, in contact with the pipe, and configured to guide the laser beam; a guide lens built in the guide pipe, and configured to adjust focus of the laser beam; a guide plate coupled with the guide pipe, formed to protrude in a lateral direction, and in contact with the pipe; and a guide belt formed to cover the guide plate and the pipe, and formed so that the guide plate is coupled with the pipe.

The ultrasonic reception unit may include: a light source unit configured to generate a laser beam; a transfer unit connected to the light source unit, and configured to transfer the laser beam; a detection unit connected to the transfer unit, mounted on the pipe, and configured to detect the laser beam; and a reception unit connected to the transfer unit, and configured to receive the laser beam and transfer information regarding the ultrasonic signal to the analysis unit.

The detection unit may include: a detection pipe connected to the transfer unit, in contact with the pipe, and configured to guide the laser beam; a detection lens built in the detection pipe, and configured to adjust focus of the laser beam; a detection filter built in the detection pipe, and configured to block infrared radiant heat coming from the pipe; a detection plate coupled with the detection pipe, formed to protrude in a lateral direction, and in contact with the pipe; and a detection belt formed to cover the detection plate and the pipe, and formed so that the detection plate is coupled with the pipe.

The transfer unit may be an optical fiber.

According to another aspect, there is provided a pipe damage detection method, including: supplying, by an ultrasonic supply unit, an ultrasonic signal to a pipe; receiving, by an ultrasonic reception unit, the ultrasonic signal of the pipe; and analyzing, by an analysis unit, the ultrasonic signal and determining whether the pipe is damaged.

The ultrasonic supply unit may change a guide point along a circumferential surface of the pipe, and the ultrasonic reception unit may change a detection point along the circumferential surface of the pipe.

When determining, by the analysis unit, of whether the pipe is damaged, includes: calculating a damage index; and analyzing an outlier based on the damage index, wherein the damage index is obtained by following equations:

$$DI(i, j) = 1 - \mathrm{maxcorr}(f_i, f_j)$$

$$\mathrm{maxcorr}(f_i, f_j) = \max_{\hat{t}} \left\{ \frac{1}{N-1} \sum_{f_i, f_j} \frac{f_i(t+\hat{t}) - \overline{f}_1)(f_j(t) - \overline{f}_j)}{\sigma_{f_1} \sigma_{f_j}} \right\}$$

where $f_i$ and $f_j$ represent measurement signals measured in two paths having the same phase, $\overline{f}_i$ represents an average value of $f_i$, $\sigma f_j$ represents standard deviation of $f_j$, N represents the number of data points in a time domain of the measured $f_j$, and $\hat{t}$ represents time delay.

The pipe damage detection apparatus and method can accurately detect the damage of a pipe which is difficult for an inspector to access because it is coated with an insulating material or buried in the ground.

The pipe damage detection apparatus and method can perform accurate detection on a pipe with a high temperature used in a nuclear power plant facility or a chemical plant facility.

BRIEF DESCRIPTION

DETAILED DESCRIPTION

Hereinafter, a radiation detector according to an embodiment of the present invention will be described in detail with reference to the accompanying drawings. Thicknesses of lines or sizes of components shown in the figures may be exaggeratedly illustrated for clarity and convenience of description. Further, the terminology described below may be defined by considering a function in the present, and may differ according to an intention or custom of a user or an operator. Accordingly, the definitions with respect to the terminology may be determined based on overall content of the present specification.

Figure 1:
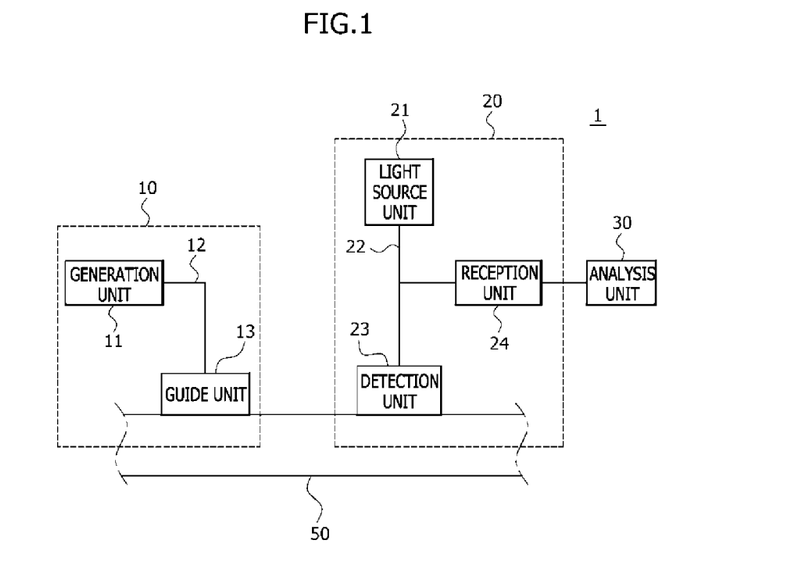
FIG. 1 is a schematic diagram illustrating a pipe damage detection apparatus according to an exemplary embodiment of the present invention.
Figure 2:
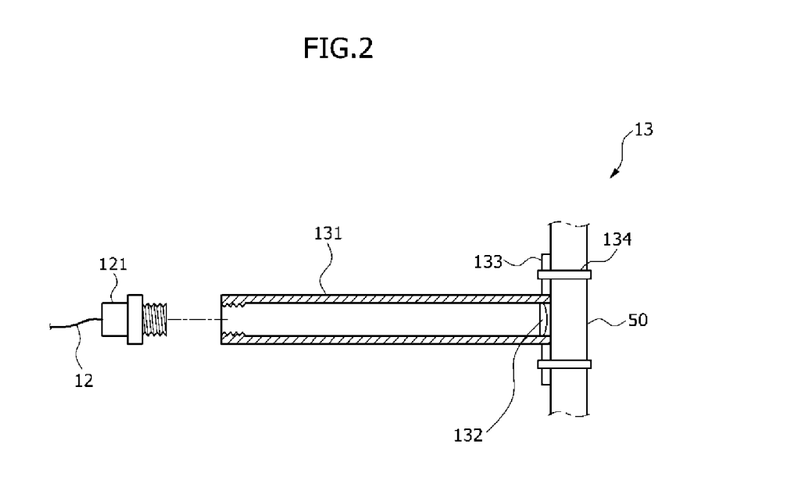
FIG. 2 is a schematic diagram illustrating a guide unit of a pipe damage detection apparatus according to an exemplary embodiment of the present invention.
Figure 3:
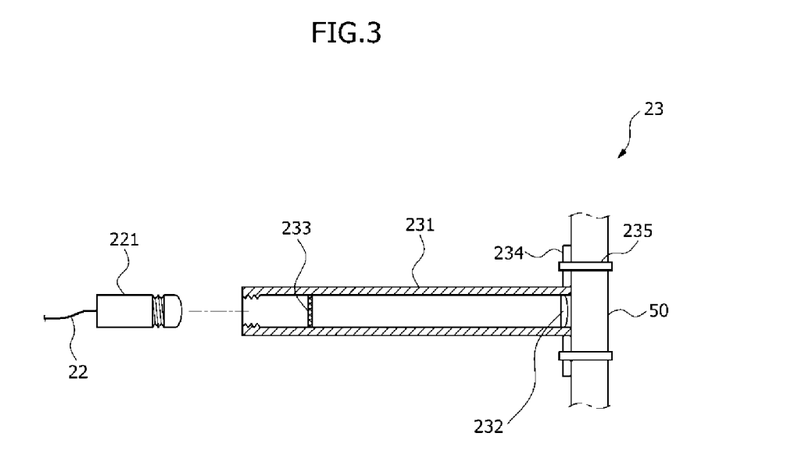
FIG. 3 is a schematic diagram illustrating a detection unit of a pipe damage detection apparatus according to an exemplary embodiment of the present invention.

FIG. 1 is a schematic diagram illustrating a pipe damage detection apparatus according to an exemplary embodiment of the present invention, FIG. 2 is a schematic diagram illustrating a guide unit of a pipe damage detection apparatus according to an exemplary embodiment of the present invention, and FIG. 3 is a schematic diagram illustrating a detection unit of a pipe damage detection apparatus according to an exemplary embodiment of the present invention.

A pipe damage detection apparatus 1 according to an exemplary embodiment of the present invention may include an ultrasonic supply unit 10, an ultrasonic reception unit 20, and an analysis unit 30.

The ultrasonic supply unit 10 may be mounted on a pipe 50, radiate a laser beam on the pipe 50, and generate an ultrasonic signal. At this time, the ultrasonic supply unit 10 may generate the ultrasonic signal along a circumferential surface at any one point of the pipe 50.

The ultrasonic reception unit 20 may radiate the laser beam on the pipe 50, and receive the ultrasonic signal of the pipe 50 included in a reflected laser beam. At this time, the ultrasonic reception unit 20 may detect the ultrasonic signal along the circumferential surface at another point of the pipe 50.

The analysis unit 30 may analyze the ultrasonic signal received by the ultrasonic reception unit 20, and determine whether the pipe 50 is damaged.

The ultrasonic supply unit 10 according to the exemplary embodiment of the present invention may include a generation unit 11, a supply unit 12, and a guide unit 13.

The generation unit 11 may generate the laser beam, and the supply unit 12 may supply the laser beam generated in the generation unit 11. One end of the supply unit 12 may be connected to the generation unit 11, and the other end of the supply unit 12 may be connected to the guide unit 13.

In this case, an optical fiber that can be survived under extreme environments such as a high temperature, radiation, corrosion, etc. may be used as the supply unit 12. Since the optical fiber itself has low resistance, the optical fiber may suppress loss of the laser beam, and may be widely used in the extreme environments.

The guide unit 13 may be mounted on the pipe 50, and guide the laser beam to the pipe 50. The guide unit 13 according to the exemplary embodiment of the present invention may include a guide pipe 131, a guide lens 132, a guide plate 133, and a guide belt 134.

The guide pipe 131 may be connected to the supply unit 12, and be in contact with the pipe 50. The guide pipe 131 may have a cylindrical shape in which the inside is hollow, and guide the laser beam.

In this case, a guide connector 121 may be provided at the other end of the supply unit 12. The guide connector 121 may be coupled with the other end of the supply unit 12 and inserted into the guide pipe 131, and may guide the laser beam to the guide pipe 131.

The guide connector 121 may have a screw thread formed on the outer surface, and may be screw-coupled with the guide pipe 131.

The guide lens 132 may be built in the guide pipe 131. The guide lens 132 may be coupled with an inner surface of the guide pipe 131, and may adjust focus of the laser beam so that the laser beam is focused on an ultrasonic guide point of the pipe 50.

The guide plate 133 may be coupled with the guide pipe 131, and formed to protrude in a lateral direction. The guide plate 133 may have a curvature corresponding to the outer surface so that the guide plate 133 is in contact with the pipe 50.

The guide belt 134 may be formed to cover the outer surfaces of the guide plate 133 and the pipe 50. The guide belt 134 may limit movement of the guide pipe 131 by fixing the guide plate 133 to be in close contact with the pipe 50.

In this case, the guide pipe 131 may be moved along the circumferential surface of the pipe 50, and the guide point of the pipe 50 may be varied.

The ultrasonic reception unit 20 according to the exemplary embodiment of the present invention may include a light source unit 21, a transfer unit 22, a detection unit 23, and a reception unit 24.

The light source unit 21 may generate the laser beam, one end of the transfer unit 22 may be connected to the light source unit 21, the other end of the transfer unit 22 may be connected to the detection unit 23, and the transfer unit 22 may transfer the laser beam.

In this case, an optical fiber with durability in extreme environments such as a high temperature, radiation, corrosion, etc. may be used as the transfer unit 22. Since the optical fiber itself has low resistance, the optical fiber may suppress loss of the laser beam and may be widely used in the extreme environments.

The detection unit 23 may be mounted on the pipe 50, and may detect the laser beam. That is, the detection unit 23 may guide the laser beam of the light source unit 21 to reach the pipe 50, and detect the laser beam reflected from the pipe 50 and including the ultrasonic signal of the pipe 50.

The reception unit 24 may be connected to the transfer unit 22, may receive the laser beam, and may transfer information regarding the ultrasonic signal of the pipe 50 to the analysis unit 30.

That is, the reception unit 24 may digitize the ultrasonic signal of the pipe 50, and transfer the digitized ultrasonic signal to the analysis unit 30. The analysis unit 30 may analyze the transferred ultrasonic signal, and determine whether the pipe 50 is damaged.

The detection unit 23 according to the exemplary embodiment of the present invention may include a detection pipe 231, a detection lens 232, a detection filter 233, a detection plate 234, and a detection belt 235.

The detection pipe 231 may be coupled with the transfer unit 22, and be in contact with the pipe 50. The detection pipe 231 may have a cylindrical shape in which the inside is hollow, and may guide the laser beam.

In this case, a detection connector 221 may be provided at one end of the transfer unit 22. The detection connector 221 may be coupled with the one end of the transfer unit 22 and inserted into the detection pipe 231, and may guide the laser beam radiated to the pipe 50 or reflected from the pipe 50 in the corresponding direction.

The detection connector 221 may have a screw thread formed on the outer surface, and the detection pipe 231 may be screw-coupled with the detection pipe 231.

The detection lens 232 may be built in the detection pipe 231. The detection lens 232 may be coupled with an inner surface of the detection pipe 231, and may adjust focus of the laser beam.

The detection filter 233 may be built in the detection pipe 231. The detection filter 233 may be coupled with the inner surface of the detection pipe 231, and may prevent heat damage by blocking infrared radiant heat coming from the pipe 50.

In this case, the detection lens 232 may be arranged adjacent to the pipe 50, and the detection filter 233 may be arranged adjacent to the detection connector 221.

The detection plate 234 may be coupled with the detection pipe 231, and formed to protrude in a lateral direction. The detection plate 234 may have a curvature corresponding to the outer surface so that the detection plate 234 is in contact with the pipe 50.

The detection belt 235 may be formed to cover outer surfaces of the detection plate 234 and the pipe 50. The detection belt 235 may limit movement of the detection pipe 231 by fixing the detection plate 234 to be in close contact with the pipe 50.

In this case, since the detection pipe 231 moves along the circumferential surface of the pipe 50, a detection point of the pipe 50 may be varied.

A pipe damage detection method according to an exemplary embodiment of the present invention having the construction described above will be schematically described below.

Figure 4:
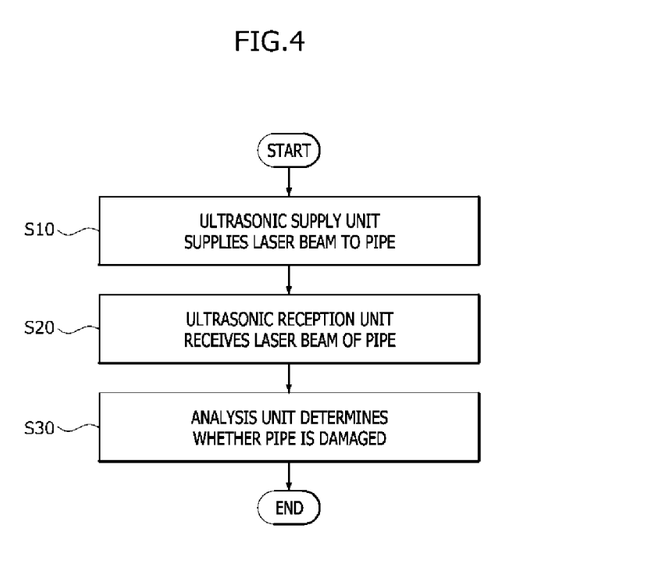
FIG. 4 is a schematic flowchart for describing a pipe damage detection method according to an exemplary embodiment of the present invention.

FIG. 4 is a schematic flowchart for describing a pipe damage detection method according to an exemplary embodiment of the present invention.

Referring to FIG. 4, the ultrasonic supply unit 10 may supply the ultrasonic signal to the pipe 50 (S10). That is, when the laser beam generated in the ultrasonic supply unit 10 reaches the guide point of the pipe 50, the ultrasonic signal may be generated in the pipe 50.

After the ultrasonic signal is supplied to the pipe 50, the ultrasonic reception unit 20 may receive the ultrasonic signal generated in the pipe 50 (S20).

After the ultrasonic reception unit 20 receives the ultrasonic signal, the analysis unit 30 may analyze the ultrasonic signal, and determine whether the pipe 50 is damaged (S30).

Figure 5:
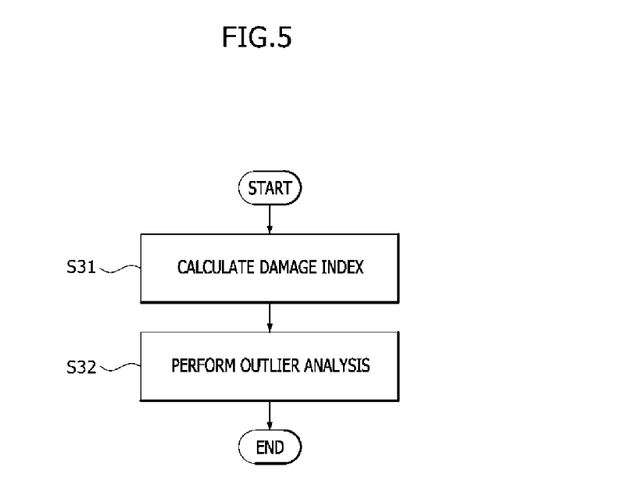
FIG. 5 is a flowchart for describing an operation in which an analysis unit detects whether a pipe is damaged in a pipe damage detection method according to an exemplary embodiment of the present invention.

FIG. 5 is a flowchart for describing an operation in which an analysis unit detects whether a pipe is damaged in a pipe damage detection method according to an exemplary embodiment of the present invention.

Referring to FIG. 5, the analysis unit 30 may calculate a damage index (DI) (S31), perform an outlier analysis based on the calculated DI, and determine whether the pipe 50 is damaged (S32).

Hereinafter, the DI and the outlier analysis will be described in detail.

The ultrasonic supply unit 10 may change the guide point along the circumferential surface of the pipe 50, and the ultrasonic reception unit 20 may change the detection point along the circumferential surface of the pipe 50.

Figure 6:
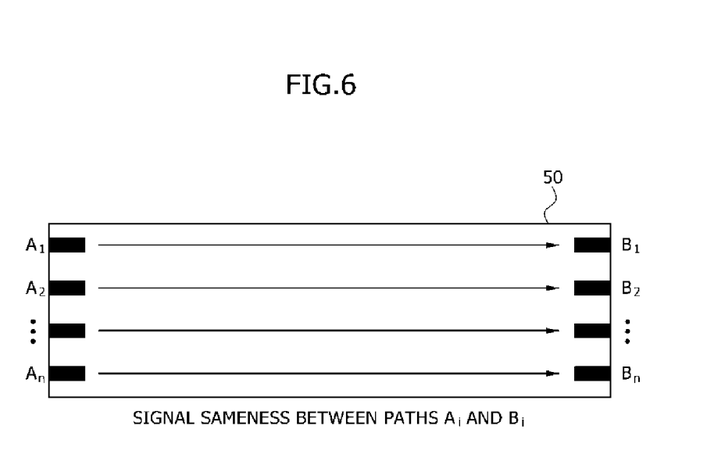
FIGS. 6 to 8 are schematic diagrams illustrating an ultrasonic signal path according to a guide point of an ultrasonic supply unit and a detection point of an ultrasonic reception unit when a pipe is not damaged in a pipe damage detection method according to an exemplary embodiment of the present invention.
Figure 7:
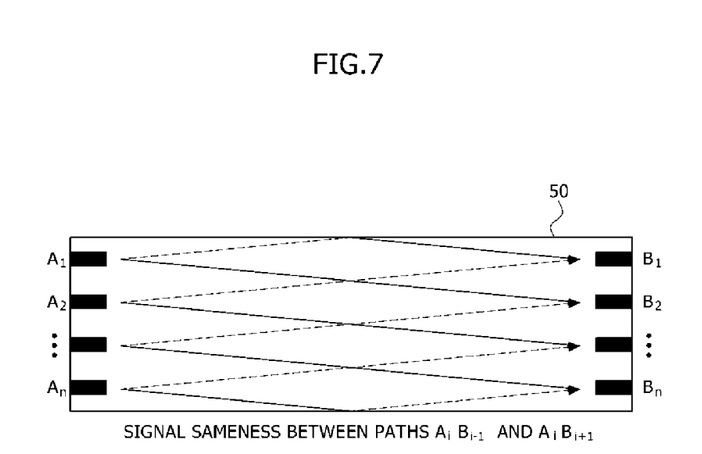
Figure 8:
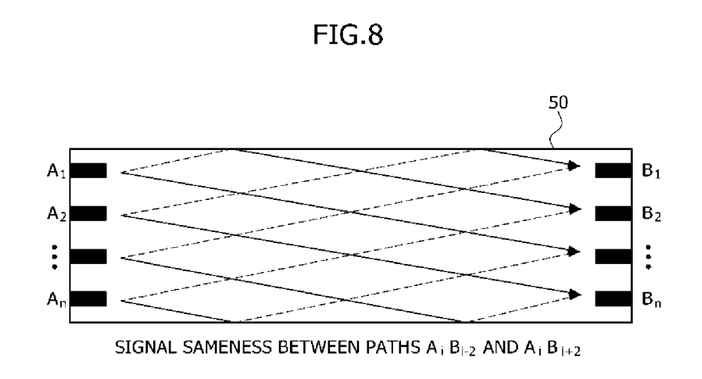

FIGS. 6 to 8 are schematic diagrams illustrating an ultrasonic signal path according to a guide point of an ultrasonic supply unit and a detection point of an ultrasonic reception unit when a pipe is not damaged in a pipe damage detection method according to an exemplary embodiment of the present invention.

Referring to FIGS. 6 to 8, when considering axial symmetry of the ultrasonic signal in a plane view of the pipe 50 without damage, every ultrasonic signal should be the same in the ultrasonic path having the same phase and the same length.

The following Equation 1 represents several examples of signal combinations showing sameness.

(a) Signal $A_1B_1$=Signal $A_2B_2$= . . . =Signal $A_{n-1}B_{n-1}$=Signal $A_nB_n$;

(b) Signal $A_1B_2$=Signal $A_2B_1$= . . . =Signal $A_{n-1}B_n$=Signal $A_nB_{n-1}$;

(c) Signal $A_1B_3$=Signal $A_3B_1$= . . . =Signal $A_{n-2}B_n$=Signal $A_nB_{n-2}$;   Equation 1

Here, $A_n$ represents various guide points, and $B_n$ represents multiple detection points.

The pipe damage detection method according to the exemplary embodiment of the present invention may use the fact that the sameness is satisfied in the pipe 50 without damage, but is not satisfied in the pipe 50 with damage.

For reference, there may be laser paths having various types of sameness according to a value of "n" in addition to Equation 1.

Meanwhile, the analysis unit 30 may calculate the DI by the following Equation 2 (S31) in the operation (S30) of determining whether the pipe 50 is damaged.

$$DI(i, j) = 1 - \text{maxcorr}(f_i, f_j) \quad \text{Equation 2}$$

$$\text{maxcorr}(f_i, f_j) = \max_{\tilde{t}} \left\{ \frac{1}{N-1} \sum_{f_i, f_j} \frac{f_i(t+\tilde{t}) - \overline{f}_i)(f_j(t) - \overline{f}_j)}{\sigma_{f_i} \sigma_{f_j}} \right\} \quad \text{Equation 3}$$

Here, $f_i$ and $f_j$ represent measurement signals measured in two paths having the same phase, $\overline{f}_i$ represents an average value of $f_i$, $\sigma f_j$ represents standard deviation of $f_j$, N represents the number of data points in a time domain of the measured $f_i$, and $\tilde{t}$ represents time delay.

That is, the DI may be a value calculated according to the sameness of the ultrasonic paths described above, and every DI may be close to 0 when the pipe 50 is not damaged.

When the pipe 50 is damaged, a combination of specific $f_i$ and $f_j$ may include the measurement signal obtained in a path passing through a damage point of the pipe 50. Accordingly, when the pipe 50 is damaged, the DI may be increased.

Meanwhile, after calculating every DI described above, it may be determined whether the pipe 50 is damaged by performing the outlier analysis (S32).

The outlier analysis may be performed by aligning every DI in ascending order and applying a probability distribution while sequentially increasing the number by one from the smallest DI (for example, from the "1st" DI to the "(m−1)-th" DI), and obtaining a threshold value.

When comparing the obtained threshold value and a next DI (for example, the "m-th" DI), the DI may be regarded as the outlier and the pipe 50 may be determined to be damaged when the DI is larger than the threshold value.

For reference, as described above, since the DI is represented as being large when there is a path with damage, the DI being regarded as the outlier may mean that the pipe 50 is damaged.

FIGS. 9 to 14 are diagrams for schematically describing an outlier analysis in a pipe damage detection method according to an exemplary embodiment of the present invention.

Figure 9:
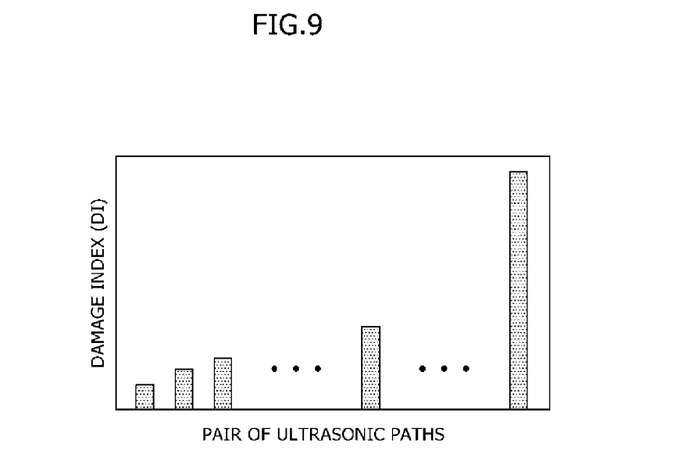
FIGS. 9 to 14 are schematic diagrams for describing a stepwise outlier analysis in a pipe damage detection method according to an exemplary embodiment of the present invention.
Figure 10:
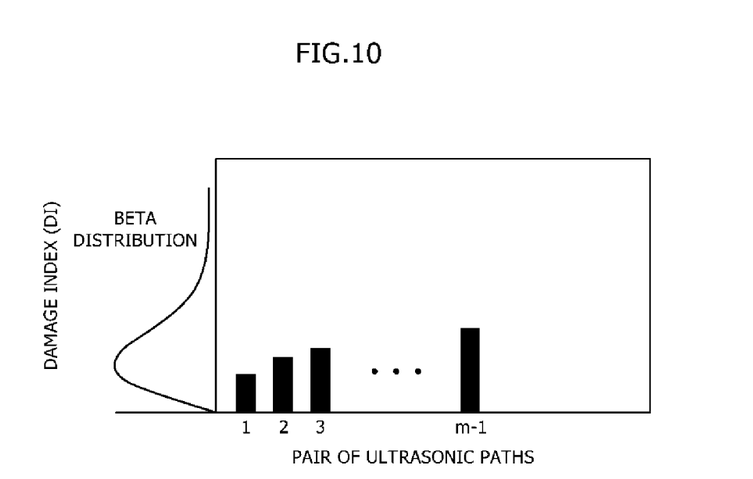

First, every DI may be aligned in ascending order (1≤m≤N) for the outlier analysis (FIG. 9).

Figure 11:
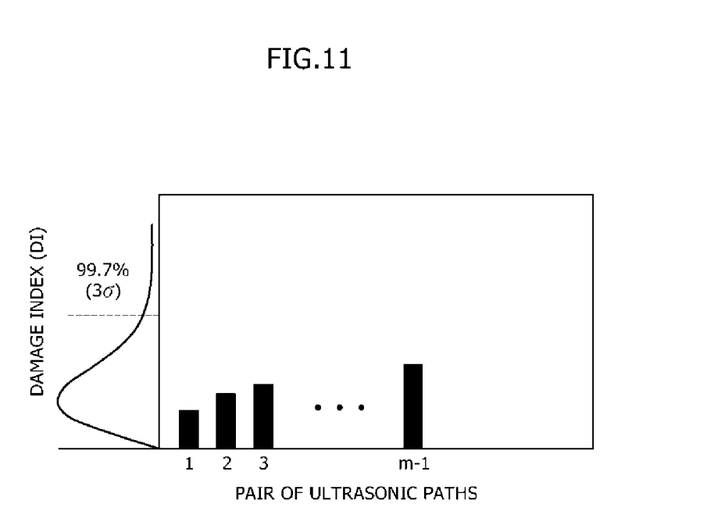
Figure 12:
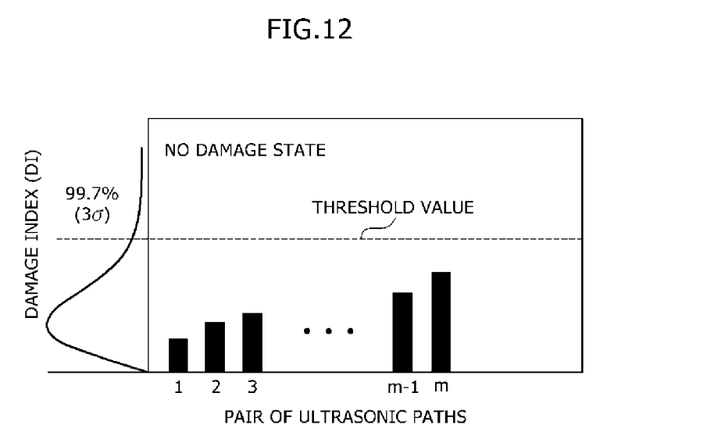

The probability distribution may be applied to the first DI to the (m−1)-th DI (FIG. 10), and the threshold value corresponding to a confidence interval which is previously defined may be calculated (FIG. 11).

In this case, the (m−1)-th DI which is first selected may be typically set as half of the number of DIs.

Figure 13:
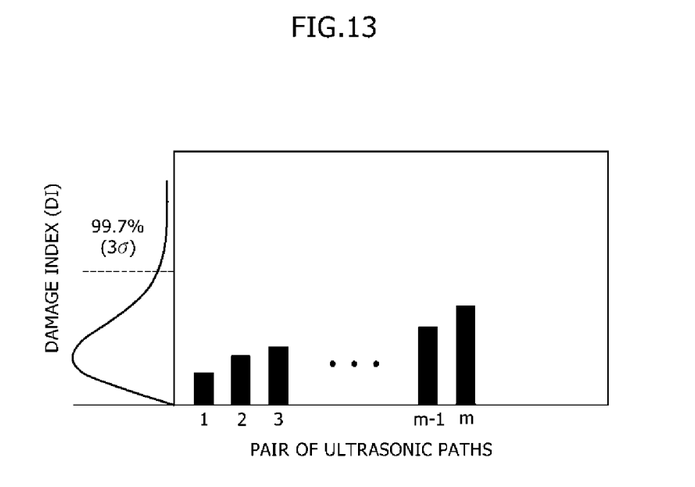

When the m-th DI is smaller than the threshold value (FIG. 12), the operations described above with reference to FIGS. 10 and 11 may be repeatedly performed in the same manner with respect to the first to m-th DIs (FIG. 13).

Figure 14:
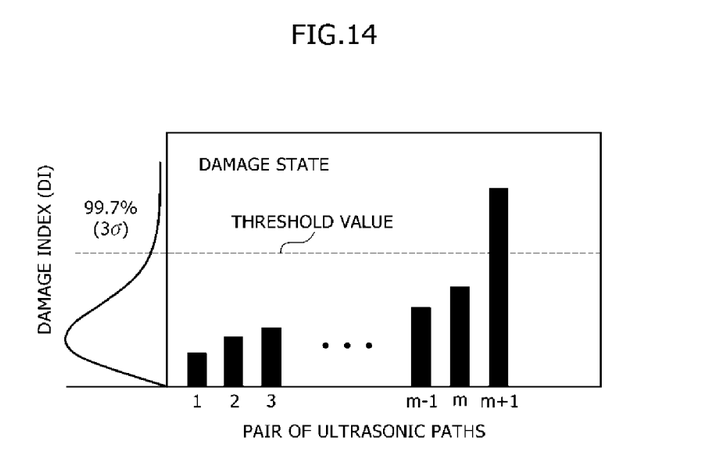

When the (m+1)-th DI is found to be larger than the threshold value by performing the operation described with reference to FIG. 13, the DIs subsequent to the (m+1)-th DI may be regarded as a value affected by every damage path (FIG. 14).

However, when every DI of the first to N-th DIs is found to be smaller than the threshold value by performing the operations described above, the pipe 50 may be determined not to be damaged.

Meanwhile, since a range of the DI is from 0 to 1, in order to imitate the distribution of the DI, a beta distribution (introduced by Hayter in 2007) given by the following Equation 4 may be introduced.

$$f(X; \alpha, \beta) = \frac{1}{B(\alpha, \beta)} x^{\alpha-1}(1-x)^{\beta-1} \qquad \text{Equation 4}$$

Here, B represent a beta functions, and α and β represent variables determining a shape of the beta distribution.

When performing a goodness-of-fit test through a Kolmogorov-Smirnov verification method (introduced by Ross in 2004), it will be known that the beta distribution may closely imitate the distribution of the DI of the pipe 50 without damage.

In this case, the threshold value may be set as a value of 99.7% (3σ) in one side of a confidence interval.

It will be apparent to those skilled in the art that various modifications can be made to the previously described exemplary embodiments of the present invention without departing from the spirit or scope of the invention. Thus, it is intended that the present invention cover all such modifications provided they come within the scope of the appended claims and their equivalents.

The invention claimed is:

1. A pipe damage detection apparatus, comprising:
an ultrasonic supply unit configured to supply an ultrasonic signal to a pipe;
an ultrasonic reception unit configured to receive the ultrasonic signal of the pipe; and
an analysis unit configured to analyze the ultrasonic signal received by the ultrasonic reception unit, and determine whether the pipe is damaged;
wherein the ultrasonic supply unit comprises:
a generation unit configured to generate a laser beam,
a supply unit including one end which is connected to the generation unit, and configured to supply the laser beam, and
a guide unit connected to the other end of the supply unit, mounted on the pipe, and configured to guide the laser beam to the pipe;
wherein the guide unit comprises:
a guide pipe connected to the supply unit, in contact with the pipe, and configured to guide the laser beam,
a guide lens built in the guide pipe, and configured to adjust focus of the laser beam,
a guide plate coupled with the guide pipe, formed to protrude in a lateral direction, and in contact with the pipe, and
a guide belt formed to cover the guide plate and the pipe, and formed so that the guide plate is coupled with the pipe.

2. The pipe damage detection unit of claim 1, wherein the supply unit is an optical fiber.

3. The pipe damage detection unit of claim 1, wherein the ultrasonic reception unit comprises:
a light source unit configured to generate a laser beam;
a transfer unit connected to the light source unit, and configured to transfer the laser beam;
a detection unit connected to the transfer unit, mounted on the pipe, and configured to detect the laser beam; and
a reception unit connected to the transfer unit, and configured to receive the laser beam and transfer information regarding the ultrasonic signal to the analysis unit.

4. The pipe damage detection unit of claim 3, wherein the detection unit comprises:
a detection pipe connected to the transfer unit, in contact with the pipe, and configured to guide the laser beam;
a detection lens built in the detection pipe, and configured to adjust focus of the laser beam;
a detection filter built in the detection pipe, and configured to block infrared radiant heat coming from the pipe;
a detection plate coupled with the detection pipe, formed to protrude in a lateral direction, and in contact with the pipe; and
a detection belt formed to cover the detection plate and the pipe, and formed so that the detection plate is coupled with the pipe.

5. The pipe damage detection unit of claim 3, wherein the transfer unit is an optical fiber.

6. A pipe damage detection method, comprising:
supplying, by an ultrasonic supply unit, an ultrasonic signal to a pipe;
receiving, by an ultrasonic reception unit, the ultrasonic signal of the pipe; and
analyzing, by an analysis unit, the ultrasonic signal, and determining whether the pipe is damaged;
wherein the ultrasonic supply unit changes a guide point along a circumferential surface of the pipe, and the ultrasonic reception unit changes a detection point along the circumferential surface of the pipe;
wherein the determining, by the analysis unit, of whether the pipe is damaged, comprises:
calculating a damage index, and
analyzing an outlier based on the damage index, wherein the damage index is obtained by following equations $$DI(i, j) = 1 - \text{maxcorr}(f_i, f_j)$$

$$\text{maxcorr}(f_i, f_j) = \max_{\tilde{t}} \left\{ \frac{1}{N-1} \sum_{f_i, f_j} \frac{f_i(t+\tilde{t}) - \bar{f}_1)(f_j(t) - \bar{f}_j)}{\sigma_{f_1} \sigma_{f_j}} \right\}$$

where $f_i$ and $f_j$ represent measurement signals measured in two paths having the same phase, $\bar{f}_i$ represents an average value of $f_i$, $\sigma f_j$ represents standard deviation of $f_i$, N represents the number of data points in a time domain of the measured $f_j$, and $\tilde{t}$ represents time delay.

\* \* \* \* \*